United States Patent
Kohlruss et al.

(12)

(10) Patent No.: US 6,457,890 B1
(45) Date of Patent: *Oct. 1, 2002

(54) DEVICE FOR CLEANING FLAT OBJECTS

(76) Inventors: Gregor Kohlruss, Pater-Eugen-Breitensteinstr. 1, D-46325 Borken (DE); Hubert Wiesner, Grüner Weg 21, D-46354 Südlohn (DE); Ulrich Lersch, Rurstrasse 10, D-50259 Pulheim (DE); Oliver Griebe, Heideweg 12, D-46414 Rhede (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/478,066

(22) Filed: Dec. 22, 1999

(51) Int. Cl.⁷ .............................................. A47L 25/00
(52) U.S. Cl. .................... 401/38; 401/123; 401/130; 401/139; 401/190; 401/207; 401/267
(58) Field of Search .............................. 401/23, 26, 38, 401/123, 130, 131–136, 139, 266, 190, 207, 267

(56) References Cited

U.S. PATENT DOCUMENTS

| 291,145 | A | * | 1/1884 | Burling | 401/139 |
| 1,217,054 | A | * | 2/1917 | Pearman | 401/207 X |
| 4,789,262 | A | * | 12/1988 | Sanchez | 401/201 |
| 5,213,430 | A | * | 5/1993 | Pandola | 401/139 X |
| 5,879,094 | A | * | 3/1999 | Lersch et al. | 401/139 |

FOREIGN PATENT DOCUMENTS

WO  WO97/30624  * 8/1997

* cited by examiner

Primary Examiner—David J. Walczak
Assistant Examiner—Kathleen J. Prunner
(74) Attorney, Agent, or Firm—Collard & Roe, P.C.

(57) ABSTRACT

A cleaning device includes a hollow body provided with at least one flat cleaning surface and at least one outlet and filling opening. The hollow body is filled with a cleaning agent or disinfectant. An absorbent cleaning material is detachably secured to the hollow body. The absorbent material includes a cleaning pad which can be separated in one piece from the hollow body.

10 Claims, 2 Drawing Sheets

DEVICE FOR CLEANING FLAT OBJECTS

Figure 1:
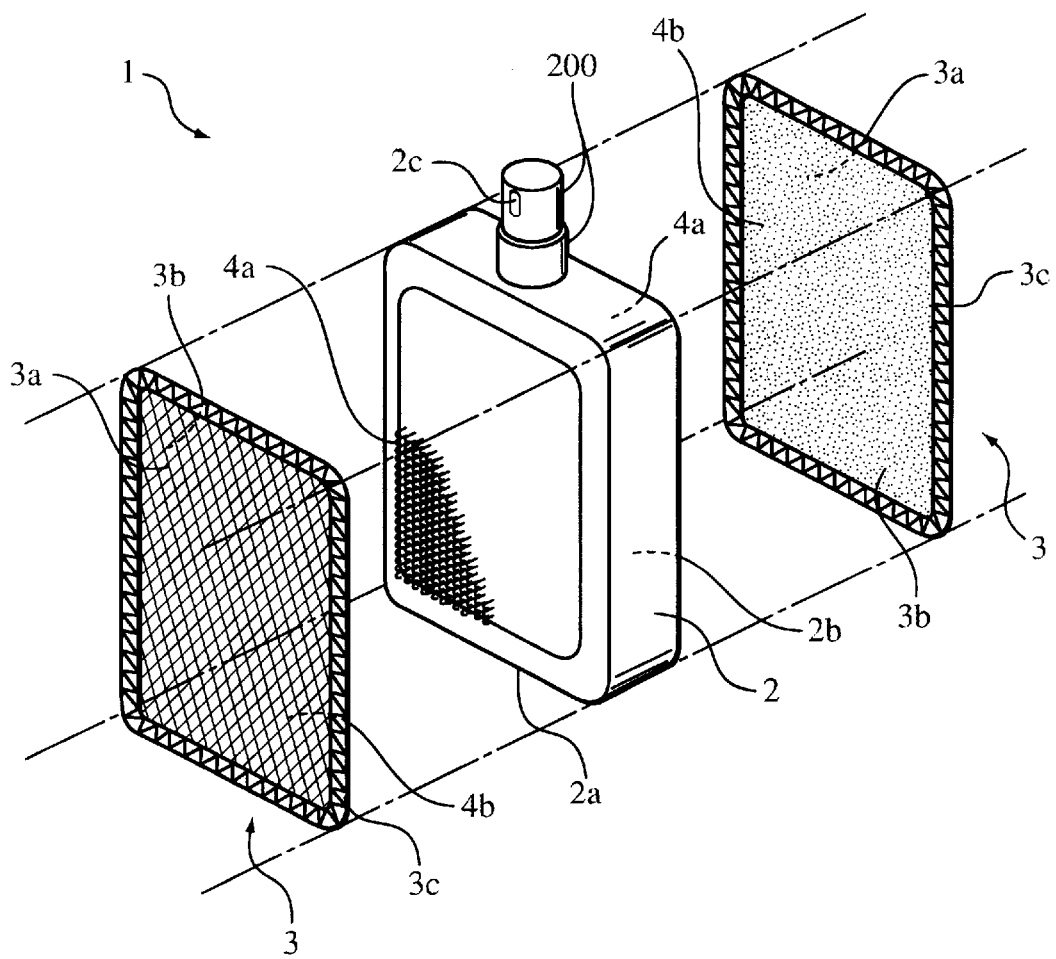

The present invention relates to a cleaning device for cleaning flat objects, in particular sterile areas in hospitals, laboratories and doctors' practices, whereby the cleaning device has a hollow body provided with at least one flat cleaning surface and at least one outlet and filling opening and filled with a cleaning agent or disinfectant, and on which an absorbent cleaning material is detachably secured.

Cleaning devices of said type representing a combination of a container for a cleaning agent and disinfectant, on the one hand, and an absorbent cleaning material on the other, are known according to the state of the art. Such cleaning devices offer the advantage that they can be handled in a simple manner and that they have a high cleaning effect. For cleaning, the cleaning agent or disinfectant is applied to the flat objects to be cleaned. Adhering dirt or dry residues of dirt can be quickly and simply removed in this way.

A cleaning device for flat objects of said type is known, for example from DE 29 25 658 Al. It has a square hollow body with an outlet and filling opening, which is filled with a cleaning agent, and it is provided with a cleaning material on two sides opposing each other. The cleaning material consists of a block of paper, the sheets of which can be individually separated from the paper block after an object has been cleaned so as to always assure a clean surface of the cleaning material. The cleaning material is absorbent so as to be capable of absorbing as much cleaning water or cleaning agent as possible and to dispense the latter in the cleaning process little by little to the flat objects to be cleaned, and to then absorb after the cleaning as much dirty water as possible from the cleaned flat objects.

The absorptive capacity of the cleaning material is based on the capillary attraction in the tissue pores of the cleaning material. In the course of the cleaning process, the absorbent cleaning material also absorbs germs picked up from the objects to be cleaned together with the dirty water and stores same in the pores of the tissue. The surface of the cleaning material is in fact kept clean by removing the top sheet of the paper block. However, the germs which penetrated the deeper layers of the cleaning material cannot be removed from the tissue pores of the cleaning material. With the known cleaning device, the germs are transferred from one object to be cleaned to the next in spite of the fact that the surface of the cleaning material appears to be clean.

This poses a serious problem in particular in sterile areas in hospitals, laboratories and doctors' offices. Sterility is the prime necessity when objects are cleaned in such areas. Pathogens have to be prevented from spreading from one sickroom to another. Ideally, this could be realized by completely omitting the absorptive capacity of the cleaning material. This, however, would substantially diminish the cleaning effect of the cleaning material. Finally, it is entirely desirable that the cleaning material, when an object has been cleaned, absorbs the dirty water with the germs from the surface of such object and leaves a clean and almost sterile surface.

When sterile areas are cleaned in hospitals, laboratories and doctors' offices, a conflict exists to a certain degree between the objectives to be accomplished, which is to have cleaning materials that have as much absorptive capacity as possible in order to absorb dirty water and germs, on the one hand, and cleaning materials with as little absorptive power as possible in order to prevent germs from getting deposited in the cleaning material, on the other.

Therefore, the problem of the present invention is to further develop a cleaning device of the type specified above for cleaning flat objects in such a way that safe removal of dirt and germs from the flat objects to be cleaned is assured, on the one hand, and that germs are prevented from spreading within sterile areas in hospitals, laboratories and doctors' practices, on the other.

For solving said problem, the invention proposes that the absorbent cleaning material consists of a cleaning pad and can be separated in one piece from the hollow body.

The cleaning pad assures on account of high absorptive capacity that dirty water and germs are safely absorbed and that the flat objects to be cleaned become clean and sterile. After a room or an area in hospitals, laboratories or doctors' offices has been cleaned, the cleaning pad is full with absorbed dirty water and germs. The germs are stored in the finest tissue pores of the cleaning pad. Only a few germs are present on the hollow body of the cleaning device, which consists of nonabsorbent material.

With the cleaning device as defined by the invention, not only the outermost, dirty layer of the cleaning material is renewed, as it is the case according to the state of the art, but all absorbent parts of the cleaning device are separated from the nonabsorbent parts, i.e., the parts loaded with germs are separated from the predominantly germ-free parts. The used cleaning pads are either cleaned, disinfected and reused, or directly disposed of as waste. The hollow body itself can be sterilized in a simple way, if need be, for example by immersing it in a disinfecting solution.

According to a preferred embodiment of the invention it is proposed that the cleaning pad has surfaces consisting of stable resistant textile fabric made of natural or synthetic fibers. Such textile cleaning pads made of stable material have a particularly good cleaning effect and can be reused particularly frequently.

Reusability of the textile cleaning pad considerably reduces the amount of waste collected in hospitals, laboratories and doctors' offices. By frequently changing the textile cleaning pad during the cleaning process it is possible to assure extreme freedom from germs without this leading to any increased amount of waste.

According to an advantageous further development of the invention it is proposed that the cleaning pad is arranged only on the cleaning surfaces of the hollow body. Cleaning pads arranged in such a way can be attached to the hollow body and removed again from the latter in a particularly easy manner. The user of the cleaning device can hold the latter in those areas which are not covered by the cleaning pad without getting the hands wet or dirty.

The cleaning device can be used in particularly many different ways if the cleaning pads have different surface materials. Such surface materials are usefully adapted to the area to be cleaned and to the type of dirt to be removed.

It has been found in practical applications that it is particularly advantageous if the hollow body is designed in the form of a square stone, and if a cleaning pad with a surface consisting of a rough scouring cloth is detachably secured on one of two cleaning surfaces opposing each other, and a cleaning pad with a surface consisting of a soft wiping cloth is detachably secured on the other of said two surfaces. Dry edges of dirt can be removed in a particularly simple manner with the rough scouring cloth. The softened dirt particles loosened from the area to be cleaned can then be picked up with the soft wiping cloth.

Therefore, the problem of the present invention is to further develop a cleaning device of the type specified above for cleaning flat objects in such a way that safe removal of the form of a sleeve extending around the entire hollow body. The sleeve is pulled as a whole over the hollow body and mounted and secured against slipping on the latter, for example by means of hook-and-loop closure, such as VEL-CRO® or adhesive elements. A cleaning pad in the form of a sleeve offers advantages especially if extreme freedom from germs is desired. When a fresh, germ-free sleeve is mounted around the hollow body, the latter is safely free of germs on all sides. Objects to be cleaned can be effectively and without problems cleaned by means of the sleeve also within the area of niches and corners.

The sleeve can be secured on the hollow body and removed again from the latter with particular ease if it has a hook-and-loop closure, such as VELCRO®. The latter advantageously extends in the longitudinal direction of the hollow body and permits opening of the sleeve, placing it around the hollow body, and securing it on the latter by closing the hook-and-loop closure, such as VELCRO®. It is also useful in this connection that slipping of the sleeve in the longitudinal direction of the hollow body is prevented when the sleeve is secured on the latter by means of a VELCRO® closure.

The cleaning device with the sleeve can be used in particularly many different ways if the sleeve has different surface materials within the area of the cleaning surfaces.

So that the cleaning pad can be secured on the hollow body and removed again from the latter as quickly and simply as possible, the invention proposes that the cleaning pad is detachably secured on the hollow body by means of hook-and-loop closure, such as VELCRO®.

According to a particularly advantageous further development of the cleaning device as defined by the invention it is proposed that a hook-and-loop closure, such as VEL-CRO® is glued to a cleaning surface of the hollow body. Said hook-and-loop closure has many small hooks and engages a corresponding number of small loops on the back side of the cleaning material or inner side of the sleeve. Such connection elements with loops are, for example sewn to the back side of the cleaning pad and to the inner side of the sleeve, or they are an integral component of the cleaning material itself. Of course, the elements can be arranged also in the reverse way, i.e., the element with the loops can be attached to the hollow body and the one with the hooks to the cleaning material.

According to yet another advantageous embodiment of the invention provision is made that a connection element is an integral component of a cleaning surface of the hollow body. This has the advantage that the hollow body with the Velcro connection element can be manufactured in one production operation.

Special advantages are obtained for the application of the cleaning device as defined by the invention in sterile areas in hospitals, laboratories and doctors' offices if the outlet and filling opening is designed in the form of a spray closure that can be unscrewed. This permits application of cleaning agent or disinfectant to the object to be cleaned without coming into contact with the latter and without transferring germs to the latter. With the help of the spray closure the cleaning agent or disinfectant is finely and evenly distributed over the object to be cleaned. The spray closure can be simply operated with the index finger of the hand of the user holding the cleaning device. By unscrewing the spray closure a filling opening becomes accessible, through which the cleaning agent or disinfectant can be filled in the hollow body of the cleaning device.

For the purpose of reducing the manufacturing cost of the cleaning device as defined by the invention it is advantageous if the outlet and the filling opening are designed as separate openings. In this way, the cleaning agent or disinfectant can be applied to the flat objects to be cleaned via an outlet opening arranged behind the cleaning material. The outlet openings are simple small apertures, with which the hollow body can be provided without problems. The filling opening can be designed in the form of a simple aperture as well, the latter being sealed, for example by a clip-like clamping closure.

Figure 2:
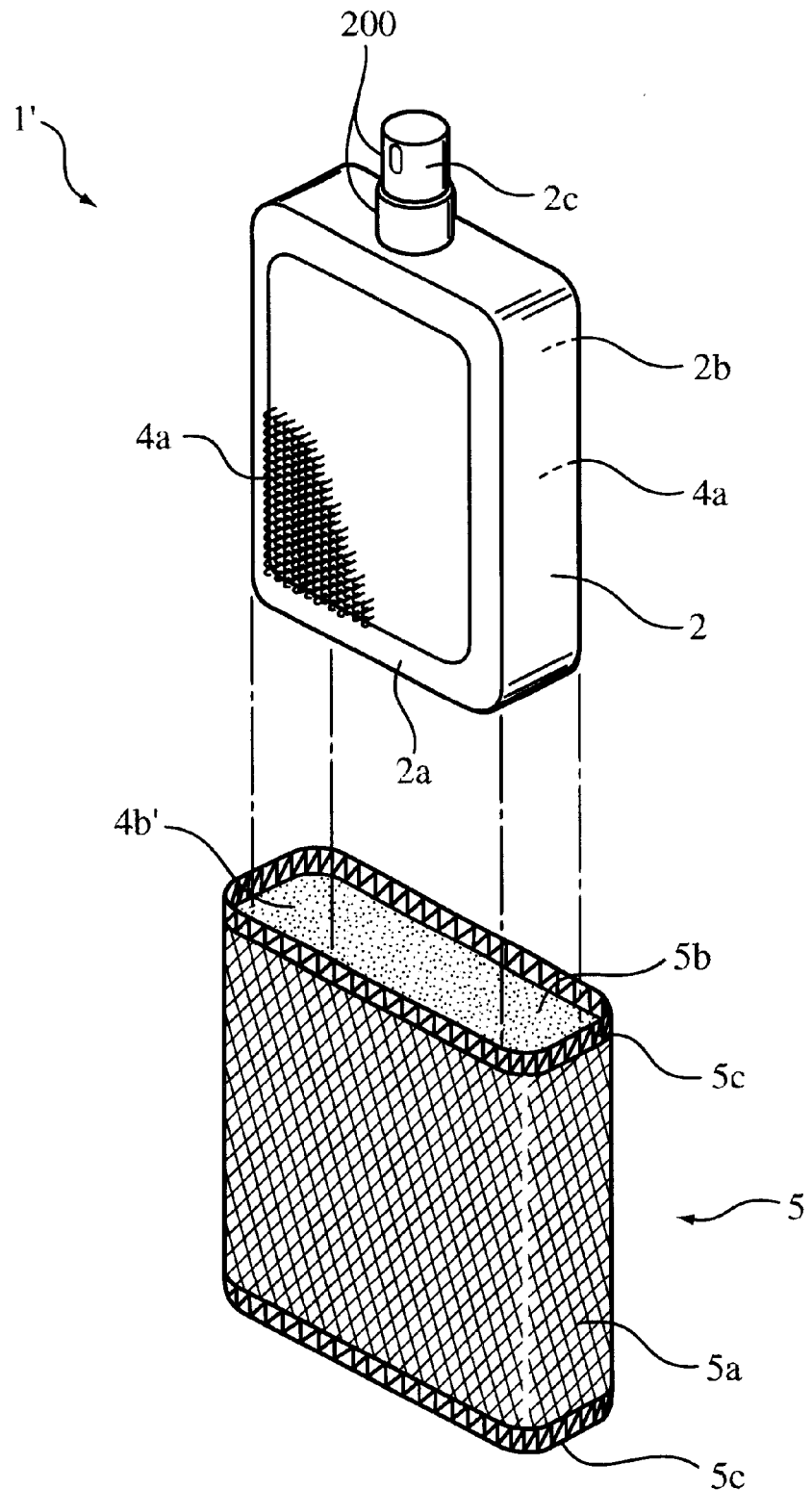

Several exemplified embodiments of the invention are explained in greater detail in the following with the help of drawings, in which FIG. 1 shows a first embodiment of the cleaning device as defined by the invention, and FIG. 2 shows a second embodiment of the cleaning device as defined by the invention.

The individual components are denoted in the drawings by identical reference symbols.

A cleaning device as defined by the invention is denoted in its entirety in FIG. 1 by reference numeral 1. It has a hollow body 2, which is filled with cleaning agent or disinfectant. Hollow body 2 has two plane cleaning surfaces 2a, 2b, which are opposing each other. In order to apply the cleaning agent or disinfectant from hollow body 2 to a flat object to be cleaned, an unscrewable spray closure 2c is arranged on hollow body 2 on the top. When spray closure 2c is unscrewed it releases a large filling opening 10 through which hollow body 2 can be filled with cleaning agent or disinfectant.

A cleaning device as defined by the invention is denoted in its entirety in FIG. 1 by reference numeral 1. It has a hollow body 2, which is filled with cleaning agent or disinfectant. Hollow body 2 has two plane or flat cleaning surfaces 2a, 2b, which are opposing each other. In order to apply the cleaning agent or disinfectant from hollow body 2 to a flat object to be cleaned, a spray closure 2c is arranged on hollow body 2 on the top. Spray closure 2c has a removable spray closure means 200 that can be screwed and unscrewed. When spray closure 2c is unscrewed it releases a large filling opening 10 through which hollow body 2 can be filled with cleaning agent or disinfectant.

In the second embodiment of cleaning device 1' as defined by the invention shown in FIG. 2, the cleaning pad is in the form of a sleeve 5. It consists of an outer surface material 5a made of a rough scouring cloth or of a soft wiping cloth, and an inner textile fabric 5b, in which small loops 4b' of connection element 4b' are integrated. Inner textile fabric 5b and outer surface material 5a are connected with each other by means of a seam 5c extending along their edges. Sleeve 5 is pulled over hollow body 2 from the top or from the bottom and secured on the latter against slipping by means of connection elements 4a, 4b'.

What is claimed is:

1. A cleaning device, comprising
   (a) a hollow body comprising at least one flat cleaning surface and being filled with cleaning agent or disinfectant;
   (b) a spray closure that can be unscrewed arranged on said hollow body; and
   (c) an absorbent cleaning material detachably secured on said hollow body by a hook-and-loop closure, wherein the absorbent cleaning material comprises a cleaning pad that is adapted to be separated in one piece from the hollow body.

2. The cleaning device according to claim 1, wherein the cleaning pad has surfaces consisting of stable, resistant textile fabric made of natural or synthetic fibers.

3. The cleaning device according to claim 1, wherein the cleaning pad is arranged only on the cleaning surface of the hollow body.

4. The cleaning device according to claim 3 wherein the cleaning pad has different surface materials.

5. The cleaning device according to claim 4, wherein the hollow body is in the form of a square stone and the cleaning pad has a surface consisting of a rough scouring cloth detachably secured on one of two cleaning surfaces opposing each other, and a second cleaning pad with a surface consisting of a soft wiping cloth is detachably secured on the other of the two cleaning surfaces.

6. The cleaning device according to claim 1 wherein the cleaning pad is designed in the form of a sleeve and extends around the entire hollow body.

7. The cleaning device according to claim 6 wherein the sleeve has one element of the hook-and-loop closure thereon.

8. The cleaning device according to claim 6 wherein the sleeve has different surface materials within the area of the cleaning surfaces.

9. The cleaning device according to claim 1 wherein one element of the hook-and-loop closure is glued to the cleaning surface of the hollow body.

10. The cleaning device according to claim 1 wherein one element of the hook-and-loop closure is an integral component of the cleaning material itself.

* * * * *

UNITED STATES PATENT AND TRADEMARK OFFICE
CERTIFICATE OF CORRECTION

PATENT NO.    : 6,457,890 B1
DATED         : October 1, 2002
INVENTOR(S)   : Kohlruss et al.

It is certified that error appears in the above-identified patent and that said Letters Patent is hereby corrected as shown below:

Title page,
Item [30], Foreign Application Priority Data, should read:
-- Feb. 26, 1996      (DE)………………….. 196 07 209.3 --.
Insert Items [86] and [87], as follows:
-- [86]   PCT Filed:        February 26, 1997
         PCT No.           PCT/EP97/00920
         §371 Date:        December 22, 1999
   [87]   PCT Pub. No.:     WO 97/30624
         PCT Pub. Data:    August 28, 1997 --

Signed and Sealed this

Sixteenth Day of November, 2004

JON W. DUDAS
*Director of the United States Patent and Trademark Office*